US012685857B2

(12) United States Patent
Uennigmann et al.

(10) Patent No.: US 12,685,857 B2
(45) Date of Patent: Jul. 21, 2026

(54) HEART PUMP DEVICE AND OPERATING METHOD FOR A HEART PUMP DEVICE

(71) Applicant: Berlin Heart GmbH, Berlin (DE)

(72) Inventors: Benno Uennigmann, Berlin (DE); Michael Frischke, Rangsdorf (DE); Oliver Peters, Berlin (DE); Florian Jankowsky, Friedland (DE)

(73) Assignee: Berlin Heart GmbH, Berlin (DE)

( * ) Notice: Subject to any disclaimer, the term of this patent is extended or adjusted under 35 U.S.C. 154(b) by 398 days.

(21) Appl. No.: 16/610,003

(22) PCT Filed: May 11, 2018

(86) PCT No.: PCT/EP2018/062190
§ 371 (c)(1),
(2) Date: Oct. 31, 2019

(87) PCT Pub. No.: WO2018/206754
PCT Pub. Date: Nov. 15, 2018

(65) Prior Publication Data
US 2020/0061267 A1      Feb. 27, 2020

(30) Foreign Application Priority Data
May 11, 2017      (EP) ..................................... 17170710

(51) Int. Cl.
*A61M 60/50*      (2021.01)
*A61M 60/148*      (2021.01)
(Continued)

(52) U.S. Cl.
CPC ........ *A61M 60/422* (2021.01); *A61M 60/148* (2021.01); *A61M 60/178* (2021.01);
(Continued)

(58) Field of Classification Search
CPC .............. A61M 60/148; A61M 60/871; A61M 2205/33
See application file for complete search history.

(56) References Cited

U.S. PATENT DOCUMENTS 5,987,541 A * 11/1999 Hewitt ...................... H04L 5/06
710/65
6,538,986 B2 * 3/2003 Isaksson ................. H04L 5/006
370/207
(Continued)

FOREIGN PATENT DOCUMENTS

CA         2167342 C  *  3/2001    ......... A61N 1/37211
EP      3 090 767 A1    11/2016
WO   WO 2011/081626 A1    7/2011

OTHER PUBLICATIONS

International Search Report, issued in International Application No. PCT/EP2018/062190, dated Aug. 1, 2018, pp. 1-2, European Patent Office, Riiswijk, Netherlands.

*Primary Examiner* — Michael J D'Abreu
(74) *Attorney, Agent, or Firm* — Crowell & Moring LLP

(57) ABSTRACT

The application relates to a heart pump device and an operating method for a heart pump device. The proposed heart pump device comprises an implantable heart pump and a controller for controlling the heart pump. The controller and the heart pump are connected to one another by way of a line with wires. Moreover, the controller is configured to supply the heart pump with electrical power by way of a first of the wires. Furthermore, the controller and the heart pump each comprise a coupling interface. Here, electrical signals for transferring data between the controller and the heart pump are able to be coupled into the first wire or able to be coupled out of the first wire by way of these coupling interfaces.

2 Claims, 3 Drawing Sheets

(51) Int. Cl.

| | |
|---|---|
| *A61M 60/178* | (2021.01) |
| *A61M 60/216* | (2021.01) |
| *A61M 60/422* | (2021.01) |
| *A61M 60/508* | (2021.01) |
| *A61M 60/878* | (2021.01) |
| *A61M 60/88* | (2021.01) |

(52) U.S. Cl.
CPC ........ *A61M 60/216* (2021.01); *A61M 60/508* (2021.01); *A61M 60/878* (2021.01); *A61M 60/88* (2021.01); *A61M 2205/3327* (2013.01)

(56)                    References Cited

U.S. PATENT DOCUMENTS

| | | | | |
|---|---|---|---|---|
| 7,856,260 | B1 * | 12/2010 | Ryu ..................... | A61N 1/0587 600/374 |
| 2003/0065366 | A1 * | 4/2003 | Merritt ................. | A61N 1/3708 607/27 |
| 2009/0088812 | A1 * | 4/2009 | Wulfman ............... | A61N 1/056 607/9 |
| 2011/0160516 | A1 * | 6/2011 | Dague ................... | A61M 60/88 600/16 |
| 2012/0248888 | A1 * | 10/2012 | Kesler ................... | H02J 7/0029 307/104 |
| 2013/0096364 | A1 * | 4/2013 | Reichenbach ............ | A61F 2/07 600/16 |
| 2014/0128937 | A1 * | 5/2014 | Decre ............... | A61N 1/36125 607/45 |
| 2016/0064117 | A1 * | 3/2016 | Romero ................. | H01B 7/048 600/16 |
| 2018/0000344 | A1 * | 1/2018 | Melodia ............... | H04W 84/18 |

* cited by examiner

HEART PUMP DEVICE AND OPERATING METHOD FOR A HEART PUMP DEVICE

CROSS-REFERENCE TO RELATED APPLICATIONS

This application is a 371 nationalization of international patent application PCT/EP2018/062190 filed May 11, 2018, which claims priority under 35 USC § 119 to European patent application 17170710.2 filed May 11, 2017. The entire contents of each of the above-identified applications are hereby incorporated by reference.

DETAILED DESCRIPTION

Figure 1:
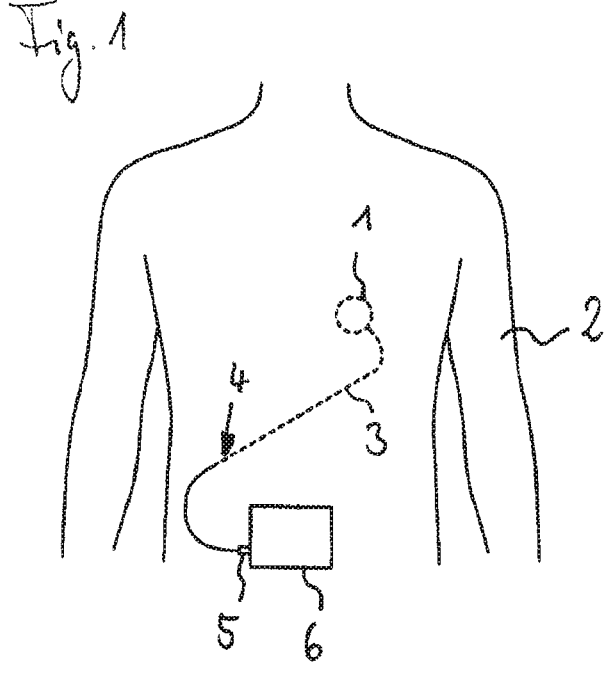
FIG. 1 shows a schematic view of a heart pump device with an implanted heart pump and an extra-corporeal controller.

The present application lies in the field of medical technology and relates to a heart pump device. In addition, the present application relates to operating method for heart pump device.

Implantable heart pumps are known from the prior art. These heart pumps are used if a heart function of a patient has to be supported or replaced. Conventional systems which are used here are what are known as VADs (ventricular assist devices). Heart pumps of this kind can be embodied for example as what are known as an LVAD (left ventricular assist device), RVAD (right ventricular assist device) or BiVAD (bi-ventricular assist device). These systems comprise not only the heart pump, which is implanted in the patient during operation, but generally also a controller, which is arranged outside the patient's body and is connected to the heart pump by way of a percutaneous line (driveline). One portion of the driveline runs outside the patient's body between the controller and a puncture site, and another portion runs inside the patient's body between the puncture site and the heart pump. The controller for example may comprise an integrated accumulator (rechargeable battery) or may be connectable to an accumulator, such that the implanted heart pump may be supplied with electrical power by the controller by way of the percutaneous line. The heart pump generally comprises a motor with a stator and a rotor provided with a blading. The motor of the heart pump generally can be driven as a result of the electrical power delivered by the controller, for example in that a flow of current is generated in windings of the stator and this sets the rotor and its blading in rotation in order to convey blood of the patient. A related system is described for example in document EP 3 090 767 A1.

An object of the present application is that of proposing an improved heart pump device. In particular, an object of the present application is to propose a heart pump device by which the well-being of a patient may be increased and damage to the skin and tissue of the patient may be reduced, wherein at the same time a complex control possibility shall be ensured for the heart pump.

The proposed heart pump device comprises an implantable heart pump and a controller for controlling the heart pump. The controller and the heart pump are connected to one another by way of a line with wires. Moreover, the controller is configured to supply electrical power to the heart pump by way of a first of the wires. In addition, the controller and the heart pump each have a coupling interface. Electrical signals are able to be coupled into the first wire or able to be coupled out of the first wire by way of these coupling interfaces in order to transfer data between the controller and the heart pump. The term "wire" describes an individual, insulated conductor for guiding current in the line, as is conventional in the field of electrical engineering. The power supply and data transfer may be implemented at the same time by way of the same wire. Since the coupling interfaces couple the electrical signals for data transfer into the power-conducting wire, it is for example not necessary to switch over, for example in alternation, between a power transfer and a data transfer by way of the wire. This wire typically connects the controller directly to the heart pump. Generally, there are no further devices connected between the heart pump and the controller. The term "line" here describes typically a combination of one or more wires which are connected to one another physically, but not necessarily electrically.

In an operating method for a heart pump device as described above or below, the electrical power is transferred from the controller to the heart pump by way of the first wire. In addition, an electrical signal is coupled into the first wire by the coupling interface of the controller or the coupling interface of the heart pump in order to transfer data between the controller and the heart pump. The electrical signal is then coupled out of the first wire by the coupling interface of the heart pump or the coupling interface of the controller.

The data transfer enables a complex control of the heart pump, for example on the basis of a plurality of sensor data items. The data exchanged by way of the electrical signals between the controller and the heart pump may be, for example, sensor data, patient data, patient identification data, hardware identification data, software version data, configuration data, operating parameters, error data, information regarding warning conditions, measurement data, time information, computing results, information regarding rotor position and/or motor data. Since the power supply of the heart pump and the data transfer are implemented by way of the same wire or the same wires, the line by way of which the heart pump and the controller are connected to one another may be designed with a reduced cross-section as compared to the prior art, since a smaller number of wires is necessary. Damage to a patient's tissue may thus be reduced, and the well-being of the patient may be increased.

In typical embodiments the controller is an extra corporeal controller, and therefore the line runs transcutaneously during operation of the heart pump. In this case the small cross-section of the line makes it possible for a puncture site of small cross-section to be formed in the patient's skin, with the line being guided through said puncture site. The proposed heart pump device may therefore lead to a relief of this puncture site and to a reduction of the risk of infection.

The data transfer between the controller and the heart pump is not necessarily implemented by way of the first wire only. The heart pump in addition is not necessarily supplied with electrical power exclusively by way of the first wire. By contrast, it may be provided that the data transfer or the power supply is made possible by a cooperation of the first wire with further wires. In typical embodiments the line has a second wire and/or a third wire. In this case it may be possible to supply electrical power to the heart pump by way of the first wire and the second wire and, as applicable, the third wire. It may also be provided that further electrical signals for data transfer between the controller and the heart pump are able to be coupled into the second wire and/or the third wire or able to be coupled out of the second or third wire by way of the coupling interfaces of the controller and the heart pump. The line generally has a sheathing which surrounds all wires of the line. This sheathing may be manufactured from a biocompatible material and for example may contain a plastics material, in particular PU or silicone.

The controller and the heart pump may be configured to transfer data from the heart pump to the controller by way of the coupling interfaces and by way of the first, the second and/or the third wire. In this case the heart pump transmits the electrical signals or data, which are then received by the controller. For example, it may be provided that the heart pump comprises sensors. Sensor data detected by the sensor may then be transferred from the heart pump to the controller for example in the manner described above and/or below.

Moreover, it may be provided additionally or alternatively that the controller and the heart pump are configured for the transfer of data from the controller to the heart pump by way of the coupling interfaces and by way of the first, the second and/or the third wire. In this case the controller transmits the electrical signals or data, which are then received by the heart pump. It is generally provided that the controller and the heart pump are each designed to both transmit and also receive the electrical signals and data. In typical embodiments the controller and the heart pump are configured to transfer electrical signals and/or data in both directions in the sense of a reciprocal operating mode (full-duplex operation). However, a simultaneous transfer by way of two transfer paths or a half-duplex operation are also possible.

The controller may comprise a modulator connected to the coupling interface of the controller. The modulator of the controller may be configured to modulate a carrier frequency signal for generating the electrical signals to be coupled into the first, the second and/or the third wire for data transfer to the heart pump. In further embodiments the heart pump comprises a modulator connected to the coupling interface of the heart pump. The modulator of the heart pump may be configured to modulate a carrier frequency signal for generating the electrical signals to be coupled into the first, the second and/or the third wire for data transfer to the controller. The modulator of the controller or the heart pump receives the data for example in the form of digital electrical signals. The receiving heart pump or the receiving controller generally comprises a demodulator, by which the received electrical signals are demodulated. The electrical signals are generally converted here into digital signals. The received and demodulated data are then typically transferred to a microcontroller of the heart pump or the control unit and are processed as appropriate. The modulation to the carrier frequency generated by the modulator of the heart pump and/or the controller may be implemented for example by a digital modulation process known per se, for example by an amplitude modulation (amplitude-shift keying, ASK), a frequency modulation (frequency-shift keying), a phase modulation (phase-shift keying) or by mixed forms. In particular, components that use an ASK process for modulation or demodulation may be implemented in a particularly simple and space-saving manner. The modulators and/or demodulators are formed in typical embodiments by circuits of appropriate design, but may also be implemented on the basis of software.

The controller may be configured to couple a carrier frequency signal into a wire or a plurality of the wires of the line, for example into the first, the second and/or the third wire, by way of the coupling interface of the controller. The heart pump is configured in some embodiments to couple out the carrier frequency signal by way of the coupling interface of the heart pump. The modulator of the heart pump may also be configured to modulate the carrier frequency signal for generating the electrical signals to be coupled into the first, the second and/or the third wire for data transfer to the heart pump. In this way, data transfer from the heart pump to the controller by means of modulated carrier frequency is made possible, without the need to generate the carrier frequency in the heart pump. The component requirement on the part of the implantable heart pump may thus be kept low, and the hart pump may also be configured so as to be particularly compact. If, at the same time, data is transferred from the controller to the heart pump, another carrier frequency is then generally used by the modulator of the control unit, such that interference caused by crosstalk between the two transfer directions is avoided.

In order to supply the heart pump with electrical power, the first, the second and/or the third wires are typically connected to a power supply, in particular a current and/or voltage source, of the controller. For example, it may be provided that the controller comprises a receptacle for a mains plug, a primary battery and/or an accumulator, by way of which the controller may be supplied with electrical power. Electrical power may be supplied in this way typically also to the heart pump by way of the first, the second and/or the third wire.

The supply of electrical power to the heart pump may be provided for example in order to supply sensors in the heart pump and/or further electronic components of the heart pump with direct current and/or with alternating current. It may be provided additionally or alternatively that the first wire, the second wire and/or the third wire are/is connected to a motor of the heart pump, in particular to a stator of the motor. It may be possible to supply the heart pump with the electrical power, in particular with direct current and/or with alternating current, via the first wire, the second wire and/or the third wire in order to convey blood of a patient.

In typical embodiments the controller is configured to supply the heart pump in such a way that the first, the second, and the third wire each guide one of three motor currents which are phase-shifted in relation to one another. The motor of the heart pump may be embodied as a synchronous motor, for example. The rotary frequency of the rotor inclusive of a blading optionally connected to the rotor, and therefore the conveyed quantity of blood, may be defined here by the frequency of the alternating current.

The carrier frequency signal in typical embodiments has a frequency of at least 1 MHz and/or at most 10 MHz, for example 5 MHz or 6 MHz. This frequency range is particularly suitable for avoiding interference between the electrical signals for the data transfer and alternating currents for the energy transfer to the heart pump.

The heart pump may furthermore comprise a location modulator. It may be provided that the location modulator is configured to receive a carrier signal and data. Furthermore, the location modulator may be configured, depending on these data, to implement a switchover between an in-coupling of the carrier signal by way of the coupling interface of the heart pump into one of two of the wires, for example between the first and the second wire or between the second and the third wire. Binary electrical signals may thus be sent to the controller by the location modulator. The location modulator generally comprises an electronic switch, by which the switchover is implemented. For example, the location modulator couples the carrier signal into the second wire if the location modular obtains a binary value "1" as data input. If, by contrast, the location modulator obtains a binary value "0" as data input, the location modulator may couple the carrier signal into the third wire.

In this way, the second wire and the third wire may each guide a binary signal, said signals being inverted in relation to one another. The carrier signal may correspond to the carrier frequency signal and/or for example may be a signal sent by the controller, for example a carrier signal modulated by the modulator of the controller or an unmodulated carrier signal. If the carrier signal is a signal modulated by the modulator of the controller, in particular an ASK-modulated signal, a degree of modulation, i.e. the quotient of an amplitude corresponding to a binary value 1 and a difference between this amplitude and an amplitude corresponding to a binary value "0" is typically less than 1. Of course, the degree of modulation is generally greater than "0". As a result of the switchover implemented by the location modulator, the electrical signals are transferred redundantly over two wires from the heart pump to the controller, such that a plausibility check of the data received by the controller may be performed in the controller, and an error detection may be carried out in the controller. The susceptibility of the data transfer to interference may thus be reduced in the described way.

The controller and/or the heart pump may also comprise a converter, in particular an S2D (single-ended to differential) converter. Such a converter may be configured to generate inverted signals from the electrical signals to be transferred to the heart pump or to the controller by way of one of the wires. This non-inverted signal may be transferred by way of the one of the wires, for example the first wire. The controller or the heart pump is then typically also configured to couple the inverted signals into a further of the wires, for example into the second wire. Typically, the non-inverted electrical signal is transferred here at the same time as the inverted signal. The receiving heart pump or the receiving controller is then configured to couple out the inverted and the non-inverted signals from the wires and to analyze them differentially, for example by means of a differential amplifier. In this way, the sensitivity of the data transfer to interference may be reduced, since in-phase interference signals or useful signals cancel each other out by the differential analysis at the receiving heart pump or at the receiving controller. This may be particularly advantageous if electrical signals are at the same time transferred in the opposite direction over one or more of the wires used for the differential transfer. It may be provided that a signal from a modulator as described above, in particular an amplitude modulator, is fed to the (S2D) converter. Following the differential analysis, a resultant signal may be fed to a demodulator as described above, in particular an amplitude demodulator.

For example, the heart pump or the controller may be configured in further embodiments to couple non-inverted signals, which are to be transferred to the controller or the heart pump, into the one of the wires, for example into the first wire, and into the further of the wires, for example into the second wire, simultaneously. In this way, the signal is transferred into both wires in-phase. The in-phase signal may be analyzed at the receiving controller or at the receiving heart pump by a summing amplifier. In this way, anti-phase interfering signals or useful signals possibly present over both wires may be easily suppressed, such that a reliable data transfer is ensured. Over both wires, an anti-phase signal transfer in the outward direction and an in-phase signal transfer in the return direction may be performed, such that the data transfer is particularly robust, i.e. less susceptible to faults, on account of the canceling out of the anti-phase or in-phase signals at the receiver.

The embodiments described above and below thus enable data transfer in two directions in a simple manner with a particularly low level of interference, in particular for the case that only a limited number of wires, for example two or three, are available for data transfer. If three wires are provided for data transfer, the electrical signals may be transferred differentially in the above-described way over the first and second wires in the outward direction and as two in-phase electrical signals in the return direction. In addition, an inverted signal of the in-phase electrical signals may additionally be transferred over the third wire in the return direction. The electrical signals transferred in the return direction may also be analyzed differentially by the receiving heart pump or the receiving controller, for example by means of a differential amplifier, by analysis of a difference between the non-inverted and in-phase electrical signals and the inverted signal from the third wire. An output of the summing amplifier may then be guided to a first input of this differential amplifier, wherein the inverted signal from the third wire is guided to a second input of this differential amplifier.

With regard to the heart pump device, any described features may be transferred to the operating method for the heart pump device, and vice versa.

Exemplary embodiments will be described hereinafter with reference to the drawings.

FIG. 1 schematically shows a view of a front side of an upper body of a patient. The figure additionally shows a heart pump 1, which is implanted in the patient's body 2 in order to assist a heart function. The heart pump 1 has a motor with a drivable rotor, and the motor is arranged in an implantable, biocompatible pump housing that has been welded fluid-tight. The heart pump 1 may be embodied for example as what is known as an LVAD-system and may be arranged in the body 2 of the patient in such a way that blood from the left heart ventricle may be conveyed into the aorta by rotation of the rotor.

The heart pump 1 is connected to a transcutaneous driveline 3, which runs in part under the patient's skin. The driveline 3 is connected to a controller 6 by way of a plug 5 outside a puncture site 4. The controller 6 supplies the heart pump 1 with electrical power by way of the driveline 3.

The controller 6 in typical embodiments is worn externally on the body 2 of the patient so as to be portable. For this purpose, the controller 6 may be connected for example to a holder and may be connected by way of this holder to the patient's body 2. For example, the holder may be a belt, a carry strap, a carry case, or an adhesive connection, which is not shown in FIG. 1.

Figure 2:
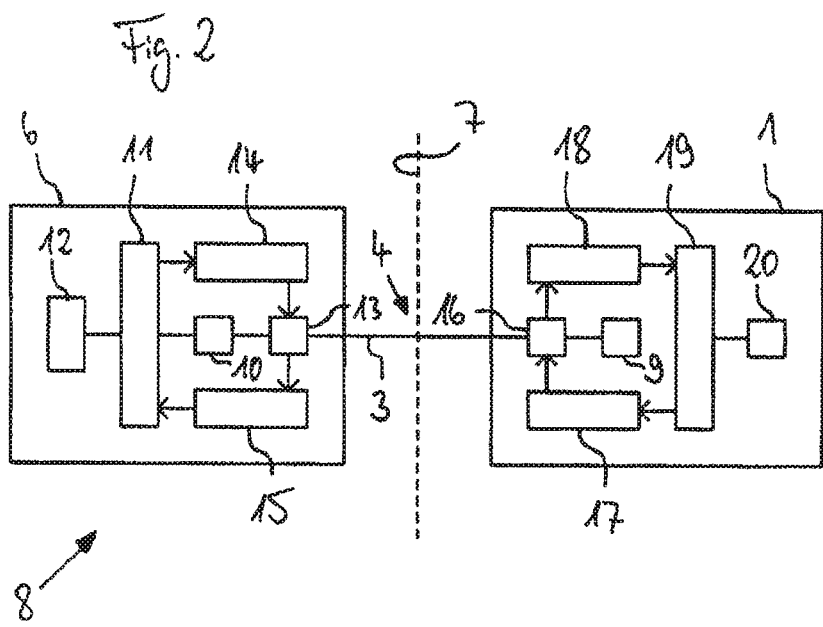
FIG. 2 shows a schematic view of the heart pump device.

FIG. 2 shows a further schematic view of the heart pump 1, the driveline 3, and the controller 6. Recurring features are provided in this figure and in the subsequent figures with the same reference signs. In addition, a skin surface 7 of the patient is shown schematically. The heart pump 1, the driveline 3 and the controller 6 form a heart pump device 8 in some embodiments. A controller 6 as described above or below may also be claimed without the heart pump 1. In addition, a heart pump 1 as described above or below may also be claimed without the controller 6.

The heart pump 1 comprises the motor 9, which is connected in the shown example to the driveline 3, such that the motor 9 may be supplied with power by the controller 6 in order to convey blood of the patient. For this purpose, the motor 9 generally comprises a stator and the rotor mounted rotatably in the stator. The rotor generally has a blading for conveying the blood. Windings of the stator are generally electrically connected here to the driveline 3 in order to supply power to the motor, and therefore the windings of the stator may be supplied with current from the controller 6. Alternatively or additionally to the power supply of the motor 9, it may be provided that further electronic components of the heart pump 1 may be supplied with electrical power by way of the driveline 3.

The driveline 3 is connected, on the side of the controller 6, with a motor driver 10. The motor driver 10 in the shown example is additionally connected by way of a microcontroller 11 of the controller 6 to a current or voltage source 12. The current or voltage source 12 is thus configured to supply the heart pump 1, in particular the motor 9 of the heart pump 1 and/or the further electronic components of the heart pump 1, with electrical power by way of the driveline 3. The current or voltage source 12 may be for example a primary battery or accumulator, in particular a plug-in accumulator, or may be formed by a mains connection.

The controller 6 and the heart pump 1 are additionally configured to exchange data with one another by way of the driveline 3. The driveline 3 generally comprises a plurality of wires, which are surrounded by a sheathing. The data are transferred here at least by way of one wire of the driveline 3, which also guides a current for the above-described power supply of the heart pump 1. For this purpose, the controller 6 has a coupling interface 13, which is connected to the microcontroller 11 of the controller 6 by way of a modulator 14 and by way of a demodulator 15. Accordingly, the heart pump 1 also has a coupling interface 16, which is connected to a microcontroller 19 of the heart pump 1 by way of a modulator 17 and a demodulator 18. The coupling interfaces 13, 16 in some embodiments may each have at least one capacitor, such that the electrical signals for the data transfer are coupled capacitively into the wires (alternatively, inductive in-coupling is also possible). Typically, the coupling interfaces 13, 16 additionally each have a high-pass filter or a bandpass filter for suppressing low-frequency motor current signals or also for suppressing low-frequency interfering signals.

In the shown example the microcontroller 19 is additionally connected to one or more sensors, as illustrated schematically by reference sign 20. By way of the coupling interface 15 of the heart pump 1, data such as sensor data or error data obtained by the sensor 20 may be modulated onto the wire of the driveline 3, i.e. coupled into this wire, by way of which the heart pump 1 is supplied with power simultaneously. These data may be coupled out of the wire by way of the coupling interface 13 of the controller 6, demodulated by the demodulator 15, and transferred to the microcontroller 11 of the controller 6. Accordingly, for example data regarding operating or control parameters of the motor 9 may be transferred from the microcontroller 11 of the controller 6 to the microcontroller 19 of the heart pump 1.

Whereas, in the shown example, power supply of the motor 9 by the current or voltage source 12 is shown, it is of course also possible additionally or alternatively that for example the microcontroller 19 of the heart pump 1 and/or the sensors 20 are supplied with electrical power in the described way by the current or voltage source 12 by way of the driveline 3.

Figure 3:
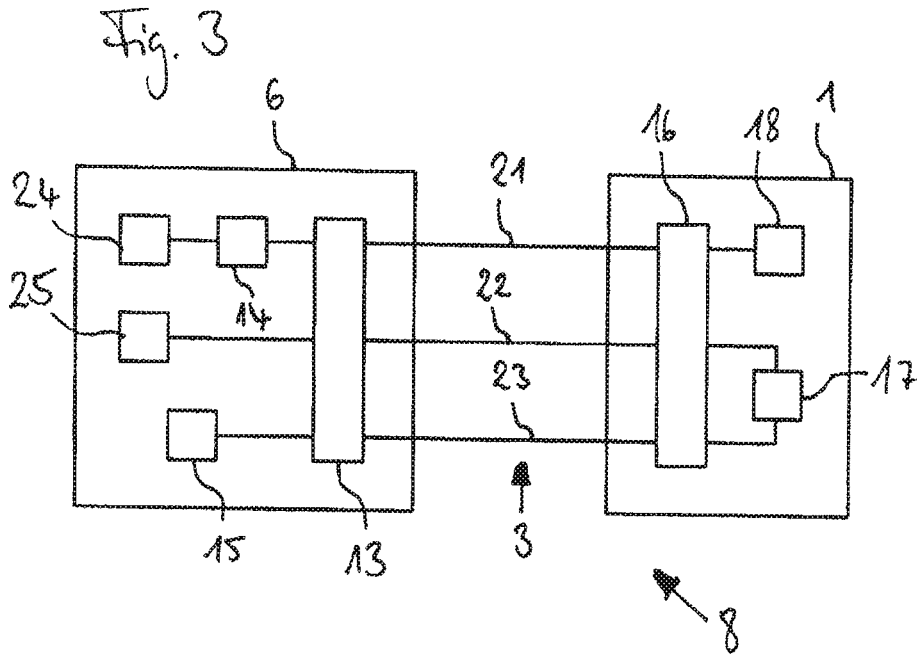
FIG. 3 shows a schematic view of a heart pump device according to a first exemplary embodiment.

A possible embodiment of the heart pump device 8, in which the data are transferred by a modulation of electrical signals onto a plurality of wires of the driveline 3, is shown in FIG. 3. Here, the signals are modulated by way of one or more carrier frequencies in addition to the electrical power supply of the heart pump 1 over the wires. The driveline 3 in the shown example has three wires, i.e. a first wire 21, a second wire 22, and a third wire 23. The heart pump 1 is supplied with electrical power by way of these wires 21, 22, 23. In some embodiments these wires 21, 22, 23 may be connected to the stator of the motor 9, guide alternating current phase-shifted in relation to one another, and thus form three motor phases for driving the motor 9 and for conveying the blood of the patient. For data transfer, the controller 6 comprises a first oscillator 24 for generating a first carrier frequency, and a second oscillator 25 for generating a second carrier frequency. The carrier frequencies may be generated for example in the form of a sinusoidal carrier signal.

In this exemplary embodiment data are transferred from the controller 6 to the heart pump 1 by way of the first wire 21, and data are transferred from the heart pump 1 to the controller 6 by way of the third wire 23. Two systems that are substantially independent of one another are thus provided for both transfer directions. Each of these systems consists of a transmitting unit, which modulates the data to be transferred onto one of the carrier signals, and a corresponding receiving unit, which demodulates the signal and thus outputs the data to be received. Modulation methods that are known per se may be used in principle for the modulation; for example, an ASK modulation may be provided for both transfer directions, since this may be implemented with a very low component requirement, both for modulation and for demodulation. For data transfer from the controller 6 to the heart pump 1, the first carrier frequency is modulated by the modulator 14 of the controller 6 in accordance with the data to be transmitted and is transferred to the heart pump 1 by way of the coupling interface 13 of the controller 6 and the first wire 21. Here, this modulated signal is coupled out of the first wire 21 by the coupling interface 16 of the heart pump 1 and is demodulated by the demodulator 18 of the heart pump 1, such that these data may be analyzed by the microcontroller 19 of the heart pump 1. A synchronization with a clock rate of the transmitter may be performed for a decoding at the receiver, in particular in the case of synchronous data transfer. The transfer of the data clock rate may be extracted from the data stream by way of clock recovery methods, however it may also be provided that the data clock rate is transferred explicitly. In particular in the case of asynchronous communication paths, it may also be provided that a coordination is performed by the sending of synchronization messages, for example synch bytes.

In order to keep the component requirement in the heart pump 1 to a minimum, the second carrier signal for the transfer direction from the heart pump 1 to the controller 6 is generated in the controller 6 by the second oscillator 25 and is transferred to the heart pump 1 by way of the coupling interface 13 of the controller 6. At the heart pump 6, the second carrier signal is then modulated using the modulator 17 of the heart pump 1. This modulated signal is then transferred for data transfer to the controller 6 and is demodulated by the demodulator 15 of the controller 6, such that the microcontroller 11 of the controller 6 may analyze these data. For amplitude modulation of the carrier frequencies, the modulators 14, 17 for example may each comprise a voltage splitter, by which an amplitude of the carrier frequency is modulated depending on a received binary data value. In the described embodiment two transfer media are required for the transfer of the data from the heart pump 1 to the controller 6. Consequently, two of the three wires or motor lines 22, 23 are used for this purpose. The third provided wire 23 is then used for the other transfer direction.

The electrical signals used for data transfer (both modulated and non-modulated) may be high-frequency signals. The frequency of these signals is typically greater than the alternating current frequency that is transferred for driving the motor by way of the wires 21, 22, 23. It may be provided that the same carrier frequency is used for both transfer directions. In order to avoid interference caused by capacitive coupling between the wires, however, it may also be provided that the first carrier frequency is different from the second carrier frequency. For example, a frequency of the first carrier signal may be 5 MHz, whereas a frequency of the second carrier signal may be 6 MHz.

Figure 4:
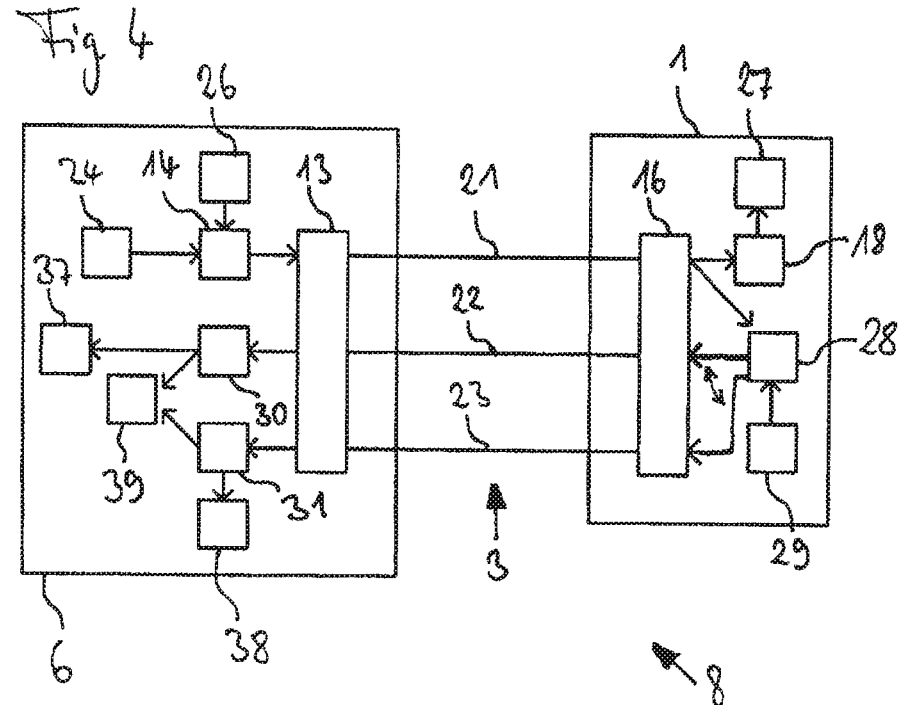
FIG. 4 shows a schematic view of a heart pump device according to a second exemplary embodiment.

A further exemplary embodiment of the heart pump device 8 is shown schematically in FIG. 4. In this embodiment, similarly to the example described above, no carrier frequency is generated in the heart pump 1, which typically has a space-saving design. By contrast, in accordance with this embodiment, merely an individual oscillator 24 is necessary for generating a carrier frequency, wherein the carrier frequency signal generated by this oscillator 24 is used for both transfer directions. This oscillator 24 is embodied as part of the controller 6 and may be configured as described above.

The data transfer from the controller 6 to the heart pump 1 in this example may be implemented as described above, wherein data to be transferred to the heart pump 1 are fed by way of a data input 26 of the controller 6 to the modulator 14 of the controller 6 and are transmitted as modulated signals to the demodulator 18 of the heart pump 1 by way of the first wire 21 and are also transferred to a data output 27 of the heart pump 1. Here, the signal may be transferred in amplitude-modulated form, wherein the degree of modulation should be selected to be less than one, such that the signal transfer to the heart pump 1 does not at any point have the amplitude zero and as described below may be used further as carrier signal for the reverse transfer direction.

In order to transfer data from the heart pump 1 to the controller 6, the heart pump 1 has a location modulator 28. The location modulator 28 is connected to the coupling interface 16 of the heart pump 1 and is connected to a data input 29 of the heart pump 1. Besides the binary data received from the data input 29 and to be transferred to the controller 6, the location modulator 28 receives the modulated carrier signal, transferred by way of the first wire 21, from the coupling interface 16 of the heart pump 1. Depending on the received data value, the location modulator 28 transfers the modulated carrier signal back to the controller 6 over one of the two other wires or over both other wires 22, 23 and thus switches over between a coupling into the second wire 22 or into the third wire 23 depending on the received data value. If the location modulator 28 for example receives a logical "1" at the data input 29, this may then forward for example the received carrier signal into the second wire 22. If the location modulator 28 by contrast receives a logical "0" at the data input 29, this may then forward for example the received carrier signal into the third wire 23.

For demodulation, at the controller 6, of the electrical signals modulated by the location modulator 28 the signals received by way of the two wires 22, 23 may be amplitude-modulated. For this purpose, the controller 6 has a first amplitude demodulator 30 and a second amplitude demodulator 31. The first amplitude demodulator 30 outputs the binary data to be received, this being shown schematically by reference sign 37. The second amplitude demodulator 31 by contrast outputs an inversion of these data, this being shown schematically by reference sign 38. It may additionally be provided that the signals output by the amplitude demodulators 30, 31 are then fed to a differential amplifier 39 for differential analysis of the data received by the controller 6. Here, envelope curves of the signals received by way of the two wires 22, 23 may be subtracted from one another, such that the desired useful signal thus results.

The controller 6 may additionally comprise a decision logic (not shown), to which the signals output by the amplitude demodulators 30, 31 are fed. In this way, any potential errors may be identified at the time of demodulation or at the time of transfer. In addition, a failure of one of the amplitude demodulators 30, 31 may be compensated for by the described transfer over two wires 22, 23 and subsequent respective demodulation.

Figure 5:
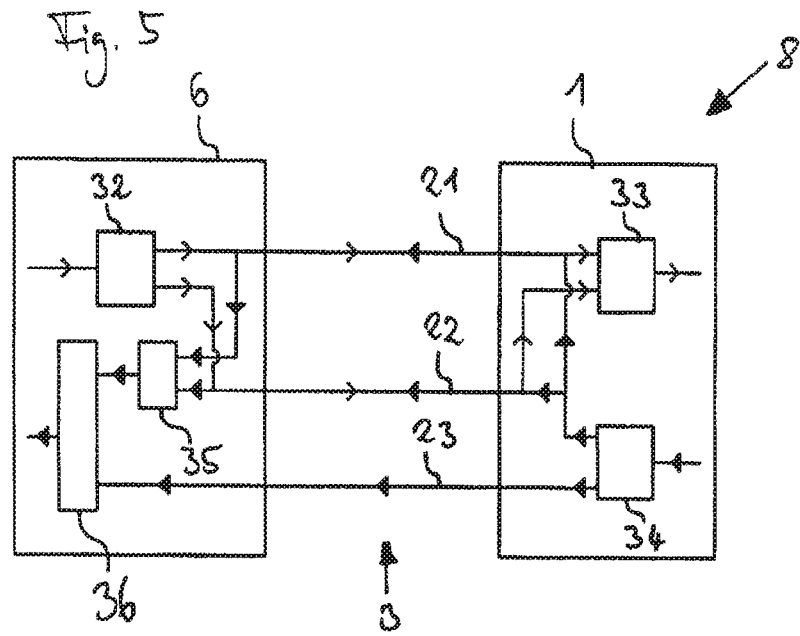
FIG. 5 shows a schematic view of a heart pump device according to a third exemplary embodiment.

A further exemplary embodiment of the heart pump device 8 is shown in FIG. 5. This embodiment differs from the above-described embodiments in that both transfer directions are constructed differentially. Firstly, as described above, a carrier signal is generated in the controller 6 and is then modulated, in particular amplitude-modulated, for data transfer to the heart pump 1. The modulated signal is then converted into a differential signal by way of an S2D converter 32 (single-ended to differential converter). This differential signal is coupled into two of the three wires 21, 22, in such a way that the first wire 21 guides the modulated signal and the second wire 22 guides a signal that is inverted in relation thereto. These signals are coupled out and analyzed differentially at the heart pump 1. To this end, the signals may be analyzed or demodulated for example using a differential amplifier 33 or a differential demodulator respectively.

For the data transfer from the heart pump 1 to the controller 6, a further carrier signal is generated and modulated, in particular amplitude-modulated, in the heart pump 1 with an oscillator. The frequency of this carrier signal differs here from the frequency of the carrier signal which is generated in the controller 6. The modulated signal is converted by way of an S2D converter 34 of the heart pump 1, transferred to the controller 6, and lastly, similarly to that described above, analyzed differentially using a differential amplifier 36 of the controller 6. Since four transfer channels are required for two differential transfer directions and only three wires 21, 22, 23 connecting the controller 6 to the heart pump 1 are provided in the shown example, at least one wire must be used for signal transfer in two directions. In the shown exemplary embodiment both the first wire 21 and the second wire 22 are used for a bidirectional signal transfer. In order to avoid interference, the coupling interface 16 of the heart pump 1 is configured to couple signals delivered from the S2D converter 34 of the heart pump 1 in-phase into the first wire 21 and the second wire 22, such that these signals are transferred redundantly. In addition, the S2D converter 34 of the heart pump 1 delivers an inverted signal to the coupling interface 16, which couples this into the third wire 23 for transfer to the controller 6.

The signals transferred to the controller 6 by way of the first wire 21 and the second wire 22 are coupled out of the wires 21, 22 by the coupling interface 13 of the controller 6 and are fed to a summing amplifier 35 of the controller 6. An output signal of this summing amplifier 35 is then guided for differential analysis to the differential amplifier 36 of the controller 6, which additionally receives the inverted signal coupled out of the third wire 23. In a third step the signal output from the differential amplifier 35 may be demodulated, such that the data are transferred in full to the controller 1. Since the electrical signals transferred over the first wire 21 and the second wire 22 to the heart pump 1 are anti-phase (inverse or asynchronous) and the data transferred over these wires 21, 22 to the controller are in-phase (non-inverted or synchronous), a mutual interference influencing the electrical signals transferred over these wires 21, 22 may be prevented by a differential analysis at the heart pump 1 or a summing analysis at the controller 6.

Features of the various designs disclosed merely in the exemplary embodiments may be combined with one another and claimed individually.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A heart pump device comprising:
an implantable heart pump;
a line comprising a plurality of wires, the wires including a first wire and a second wire; and
a controller for controlling the heart pump;
wherein the controller and the heart pump are connected by the line, and the controller is configured to supply the heart pump with electrical power through the first wire, wherein the first wire is configured to pass through a skin surface;
wherein the controller and the heart pump each comprise a coupling interface, wherein the coupling interface of the controller and the coupling interface of the heart pump are each configured to communicate electrical signals for data transmission through the first wire between the controller and the heart pump; and
wherein the heart pump comprises a location modulator, wherein the location modulator is configured to receive a carrier signal and data and, depending on this data, the location modulator is configured to implement a switchover between an in-coupling of the carrier signal via the coupling interface of the heart pump into the first wire and an in-coupling of the carrier signal via the coupling interface of the heart pump into the second wire of the line.

2. A heart pump device comprising:
an implantable heart pump comprising a location modulator;
a line comprising a plurality of wires, the wires including a first wire and a second wire; and
a controller for controlling the heart pump,
wherein the controller and the heart pump are connected by the line, and the controller is configured to supply the heart pump with electrical power through the first wire, wherein the first wire is configured to pass through a skin surface,
wherein the controller and the heart pump each comprise a coupling interface, wherein the coupling interface of the controller and the coupling interface of the heart pump are each configured to communicate electrical signals for data transmission through the first wire between the controller and the heart pump,
wherein the location modulator is configured to receive data and, depending on this data, the location modulator is configured to implement a switchover between an in-coupling of a carrier signal via the coupling interface of the heart pump into the first wire and an in-coupling of the carrier signal via the coupling interface of the heart pump into the second wire of the line.

* * * * *